United States Patent
Lansalot-Matras et al.

(10) Patent No.: US 9,518,075 B2
(45) Date of Patent: Dec. 13, 2016

(54) GROUP 5 CYCLOPENTADIENYL TRANSITION METAL-CONTAINING PRECURSORS FOR DEPOSITION OF GROUP 5 TRANSITION METAL-CONTAINING FILMS

(71) Applicant: L'Air Liquide, Société Anonyme pour l'Etude et l'Exploitation des Procédés Georges Claude, Paris (FR)

(72) Inventors: Clément Lansalot-Matras, Seoul (KR); Wontae Noh, Seoul (KR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 426 days.

(21) Appl. No.: 14/106,241

(22) Filed: Dec. 13, 2013

(65) Prior Publication Data

US 2014/0106071 A1    Apr. 17, 2014

(51) Int. Cl.
C07F 9/00       (2006.01)
C07F 17/00      (2006.01)
C23C 16/18      (2006.01)

(52) U.S. Cl.
CPC .................. *C07F 17/00* (2013.01); *C07F 9/00* (2013.01); *C23C 16/18* (2013.01)

(58) Field of Classification Search
CPC .............. C07F 17/00; C07F 9/00; C23C 16/18
USPC .......................... 556/43; 427/255.394, 255.6
See application file for complete search history.

(56) References Cited

U.S. PATENT DOCUMENTS 6,969,539 B2    11/2005  Gordon et al.

FOREIGN PATENT DOCUMENTS

WO           00/67300 A1      11/2000

OTHER PUBLICATIONS

Gibson et al., Dalton Transactions, vol. 23, pp. 4457-4465 (2003).*
Blanquart, T., et al.; "Evaluation and Comparison of Novel Precursors for Atomic Layer Deposition of Nb2O5 Thin Films"; Chem. Mater. 2012, 24 (6), pp. 975-980; ASC Publications.
Chiu, H-T., et al.; "Metal-Organic CVD of Tantalum Oxide from tert-Butylimidotris (diethylamido) tantalum and Oxygen"; Chem. Vap. Deposition 2000, 6, No. 5; pp. 223-225; Wiley-VCH Verlag GmbH.
Forsgren, K.. et al; "Halide Chemical Vapour Deposition of Ta2O5"; Thin Solid Films 1999; pp. 343-334; 111-114; Elsevier Science S.A.
Kim, H.; "Atomic layer deposition of metal and nitride thin films: Current research efforts and applications for semiconductor device processing"; J. Vac. Sci. Technol. B 21(6); Nov./Dec. 2003; pp. 2231-2261; American Vacuum Society.
Knapas, K., et al.; "Etching of Nb2O5 Thin Films by NbCl5"; Chem. Vap. Deposition 2009, 15; pp. 269-273; Wiley-VCH Verlag GmbH.
Kukli, K., et al.; "Niobium Oxide Thin Films Grown by Atomic Layer Epitaxy"; Chem. Vap. Deposition 1998, 4, No. 1; pp. 29-34; Wiley-VCH Verlag GmbH.
Lintanf-Salaun, A., et al.; "Atomic layer deposition of tantalum oxide thin films for their use as diffusion barriers in microelectronic devices"; Microelectronic Engineering 87 (2010); pp. 373-378; Elsevier B.V.
Song, M-K., et al.; "Formation of Tantalum Carbide and Nitride Phases in Atomic Layer Deposition Using Hydrogen Plasma and tert-Butylimido-tris (diethylamido)-tantalum (TBTDET), and its Effects on Material Properties"; Chem. Vap. Deposition 2008, 14; pp. 334-338; Wiley-VCH Verlag GmbH.
Yotsuya, T., et al.; "Novel Highly Volatile MOCVD Precursors for Ta2O5 and Nb2O5 Thin Films"; ECS Transactions 2008; 16 (5); pp. 243-251; The Electrochemical Society.

* cited by examiner

*Primary Examiner* — Porfirio Nazario Gonzalez
(74) *Attorney, Agent, or Firm* — Patricia E. McQueeney (57) ABSTRACT

Transition metal-containing precursors are disclosed. Also disclosed are methods of synthesizing and using the disclosed precursors to deposit transition metal-containing films on one or more substrates via a vapor deposition process.

20 Claims, 2 Drawing Sheets

GROUP 5 CYCLOPENTADIENYL TRANSITION METAL-CONTAINING PRECURSORS FOR DEPOSITION OF GROUP 5 TRANSITION METAL-CONTAINING FILMS

TECHNICAL FIELD

Disclosed are Group 5 transition metal-containing precursors. Also disclosed are methods of synthesizing and using the disclosed precursors to deposit Group 5 transition metal-containing films on one or more substrates via vapor deposition processes.

BACKGROUND

In the research of semiconductor, coatings, memories, and displays, the precursor plays an important role to obtain high quality thin films. It controls many parameters and eventually it will affect properties of thin films. The precursors require high purity, high thermal stability, high volatility, appropriate reactivity and low toxicity. Additionally, in processes of thin films, the precursors should vaporize in a limited time and at a reproducible rate for Chemical Vapor Deposition (CVD) or Atomic Layer Deposition (ALD).

In semiconductor areas, Group 5 transition metal-containing films have long been thought for variety of applications. The resistance switching characteristics of MxOy thin films show its potential applications for the next generation non-volatile resistive random access memory (ReRAM) devices as well as for high-k capacitor applications such as a thin layer in-between $ZrO_2$ layers to reduce leak current and stabilize the phase.

Typical Group 5 transition metal halides have been explored for the deposition of $M_xO_y$ (M=Nb, Ta x=1-2; y=1-5) by CVD (Thin Solid Film 1999, 343-344,111) or ALD (J. Vac. Sci. Technol. B 2003, 21, 2231, CVD 2009, 15, 269). Those precursors sometimes require high temperature and may not be appropriate as precursors due to etching effects.

$Nb(OEt)_5$ precursor has shown promising results to deposit amorphous $Nb_2O_5$ by ALD with a stable temperature windows of 230-260° C.) (CVD 1998, 4, 29). In addition, the precursor has been used to study mechanism $Nb_xO_y$ ALD depositions using $H_2O$ or $D_2O$ (Langmuir 2010, 26, 848). In case of $Ta(OEt)_5$, ALD of $Ta_2O_5$ with $H_2O$ has shown a process window between 170° C. and 230° C., having amorphous phase at 600° C., as deposited and crystalline phase at 800° C. (Microelec. Eng. 2010, 87, 373).

Imido-type precursors are probably most well known and widely used to deposit Group 5 transition metal containing films. Mostly, they are in a liquid phase with high vapor pressure, which is big advantage in industry for vaporizing and transferring to a reaction chamber. Many derivates have been studied for CVD (CVD 2008, 14, 334, CVD 2000, 6, 223, ECS Tans. 2008, 16, 243) or ALD (Chem. Mater. 2012, 24, 975).

SUMMARY

Disclosed are Group 5 transition metal-containing precursors having the formula:

Formula 1), wherein M is selected from Group 5 transition metals consisting of V, Nb, and Ta and each of $R_1$, $R_2$, $R_3$, $R_4$, and $R_5$ are independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. $R_2$ and $R_3$ can be identical or different, independently.

The disclosed Group 5 transition metal-containing precursors may further include one or more of the following aspects:
- the Group 5 transition metal-containing precursor being tert-butylimidocyclopentadienylmono(diethylamido)mono(iso-propylalkoxo)Vanadium(V);
- the Group 5 transition metal-containing precursor being tert-butylimidocyclopentadienylmono(diethylamido)mono(tert-butylalkoxo)Vanadium(V);
- the Group 5 transition metal-containing precursor being tert-butylimidocyclopentadienylmono(dimethylamido)mono(iso-propylalkoxo)Vanadium(V);
- the Group 5 transition metal-containing precursor being tert-butylimidocyclopentadienylmono(dimethylamido)mono(tert-butylalkoxo)Vanadium(V);
- the Group 5 transition metal-containing precursor being tert-butylimidomethylcyclopentadienylmono(diethylamido)mono(iso-propylalkoxo)Vanadium(V);
- the Group 5 transition metal-containing precursor being tert-butylimidomethylcyclopentadienylmono(diethylamido)mono(tert-butylalkoxo)Vanadium(V);
- the Group 5 transition metal-containing precursor being tert-butylimidomethylcyclopentadienylmono(dimethylamido)mono(iso-propylalkoxo)Vanadium(V);
- the Group 5 transition metal-containing precursor being tert-butylimidomethylcyclopentadienylmono(dimethylamido)mono(tert-butylalkoxo)Vanadium(V);
- the Group 5 transition metal-containing precursor being tert-amylimidocyclopentadienylmono(diethylamido)mono(iso-propylalkoxo)Vanadium(V);
- the Group 5 transition metal-containing precursor being tert-amylimidocyclopentadienylmono(diethylamido)mono(tert-butylalkoxo)Vanadium(V);
- the Group 5 transition metal-containing precursor being tert-amylimidocyclopentadienylmono(dimethylamido)mono(iso-propylalkoxo)Vanadium(V);
- the Group 5 transition metal-containing precursor being tert-amylimidocyclopentadienylmono(dimethylamido)mono(tert-butylalkoxo)Vanadium(V);
- the Group 5 transition metal-containing precursor being tert-butylimidocyclopentadienylmono(diethylamido)mono(iso-propylalkoxo)Niobium(V);
- the Group 5 transition metal-containing precursor being tert-butylimidocyclopentadienylmono(diethylamido)mono(tert-butylalkoxo)Niobium(V);
- the Group 5 transition metal-containing precursor being tert-butylimidocyclopentadienylmono(dimethylamido)mono(iso-propylalkoxo)Niobium(V);

the Group 5 transition metal-containing precursor being tert-butylimidocyclopentadienylmono(dimethylamido)mono(tert-butylalkoxo)Niobium(V);

the Group 5 transition metal-containing precursor being tert-butylimidomethylcyclopentadienylmono(diethylamido)mono(iso-propylalkoxo)Niobium(V);

the Group 5 transition metal-containing precursor being tert-butylimidomethylcyclopentadienylmono(diethylamido)mono(tert-butylalkoxo)Niobium(V);

the Group 5 transition metal-containing precursor being tert-butylimidomethylcyclopentadienylmono(dimethylamido)mono(iso-propylalkoxo)Niobium(V);

the Group 5 transition metal-containing precursor being tert-butylimidomethylcyclopentadienylmono(dimethylamido)mono(tert-butylalkoxo)Niobium(V);

the Group 5 transition metal-containing precursor being tert-amylimidocyclopentadienylmono(diethylamido)mono(iso-propylalkoxo)Niobium(V);

the Group 5 transition metal-containing precursor being tert-amylimidocyclopentadienylmono(diethylamido)mono(tert-butylalkoxo)Niobium(V);

the Group 5 transition metal-containing precursor being tert-butylimidocyclopentadienylmono(diethylamido)mono(iso-propylalkoxo)Tantalum(V);

the Group 5 transition metal-containing precursor being tert-butylimidocyclopentadienylmono(diethylamido)mono(tert-butylalkoxo)Tantalum(V);

the Group 5 transition metal-containing precursor being tert-butylimidocyclopentadienylmono(dimethylamido)mono(iso-propylalkoxo)Tantalum(V);

the Group 5 transition metal-containing precursor being tert-butylimidocyclopentadienylmono(dimethylamido)mono(tert-butylalkoxo)Tantalum(V);

the Group 5 transition metal-containing precursor being tert-butylimidomethylcyclopentadienylmono(diethylamido)mono(iso-propylalkoxo)Tantalum(V);

the Group 5 transition metal-containing precursor being tert-butylimidomethylcyclopentadienylmono(diethylamido)mono(tert-butylalkoxo)Tantalum(V);

the Group 5 transition metal-containing precursor being tert-butylimidomethylcyclopentadienylmono(dimethylamido)mono(iso-propylalkoxo)Tantalum(V);

the Group 5 transition metal-containing precursor being tert-butylimidomethylcyclopentadienylmono(dimethylamido)mono(tert-butylalkoxo)Tantalum(V);

the Group 5 transition metal-containing precursor being tert-amylimidocyclopentadienylmono(diethylamido)mono(iso-propylalkoxo)Tantalum(V);

the Group 5 transition metal-containing precursor being tert-amylimidocyclopentadienylmono(diethylamido)mono(tert-butylalkoxo)Tantalum(V);

Also disclosed are processes for the deposition of Group 5 transition metal-containing films on one or more substrates. At least one Group 5 transition metal-containing precursor is introduced into a reactor having at least one substrate disposed therein. At least part of the Group 5 transition metal-containing precursor is deposited onto the at least one substrate to form the Group 5 transition metal-containing film. The at least one Group 5 transition metal-containing precursor has the following formula:

Formula 1), wherein M is selected from Group 5 transition metals consisting of V, Nb, and Ta and each of $R_1$, $R_2$, $R_3$, $R_4$, and $R_5$ are independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. $R_2$ and $R_3$ can be identical or different, independently.

The disclosed processes may further include one or more of the following aspects:

introducing at least one reactant into the reactor;

the reactant being selected from the group consisting of $H_2$, $H_2CO$, $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof; and mixtures thereof;

the reactant being selected from the group consisting of: $O_2$, $O_3$, $H_2O$, $H_2O_2$, NO, $N_2O$, $NO_2$, oxygen radicals thereof; and mixtures thereof;

the Group 5 transition metal-containing precursor and the reactant being introduced into the reactor sequentially simultaneously;

the reactor being configured for chemical vapor deposition;

the reactor being configured for plasma enhanced chemical vapor deposition;

the Group 5 transition metal-containing precursor and the reactant being introduced into the chamber sequentially;

the reactor being configured for atomic layer deposition;

the reactor being configured for plasma enhanced atomic layer deposition;

the Group 5 transition metal-containing precursor being tert-butylimidocyclopentadienylmono(diethylamido)mono(iso-propylalkoxo)Vanadium(V);

the Group 5 transition metal-containing precursor being tert-butylimidocyclopentadienylmono(diethylamido)mono(tert-butylalkoxo)Vanadium(V);

the Group 5 transition metal-containing precursor being tert-butylimidocyclopentadienylmono(dimethylamido)mono(iso-propylalkoxo)Vanadium(V);

the Group 5 transition metal-containing precursor being tert-butylimidocyclopentadienylmono(dimethylamido)mono(tert-butylalkoxo)Vanadium(V);

the Group 5 transition metal-containing precursor being tert-butylimidomethylcyclopentadienylmono(diethylamido)mono(iso-propylalkoxo)Vanadium(V);

the Group 5 transition metal-containing precursor being tert-butylimidomethylcyclopentadienylmono(diethylamido)mono(tert-butylalkoxo)Vanadium(V);

the Group 5 transition metal-containing precursor being tert-butylimidomethylcyclopentadienylmono(dimethylamido)mono(iso-propylalkoxo)Vanadium(V);

the Group 5 transition metal-containing precursor being tert-butylimidomethylcyclopentadienylmono(dimethylamido)mono(tert-butylalkoxo)Vanadium(V);

the Group 5 transition metal-containing precursor being tert-amylimidocyclopentadienylmono(diethylamido)mono(iso-propylalkoxo)Vanadium(V);

the Group 5 transition metal-containing precursor being tert-amylimidocyclopentadienylmono(diethylamido)mono(tert-butylalkoxo)Vanadium(V);

the Group 5 transition metal-containing precursor being tert-amylimidocyclopentadienylmono(dimethylamido)mono(iso-propylalkoxo)Vanadium(V);

the Group 5 transition metal-containing precursor being tert-amylimidocyclopentadienylmono(dimethylamido)mono(tert-butylalkoxo)Vanadium(V);

the Group 5 transition metal-containing precursor being tert-butylimidocyclopentadienylmono(diethylamido)mono(iso-propylalkoxo)Niobium(V);

the Group 5 transition metal-containing precursor being tert-butylimidocyclopentadienylmono(diethylamido)mono(tert-butylalkoxo)Niobium(V);

the Group 5 transition metal-containing precursor being tert-butylimidocyclopentadienylmono(dimethylamido)mono(iso-propylalkoxo)Niobium(V);

the Group 5 transition metal-containing precursor being tert-butylimidocyclopentadienylmono(dimethylamido)mono(tert-butylalkoxo)Niobium(V);

the Group 5 transition metal-containing precursor being tert-butylimidomethylcyclopentadienylmono(diethylamido)mono(iso-propylalkoxo)Niobium(V);

the Group 5 transition metal-containing precursor being tert-butylimidomethylcyclopentadienylmono(diethylamido)mono(tert-butylalkoxo)Niobium(V);

the Group 5 transition metal-containing precursor being tert-butylimidomethylcyclopentadienylmono(dimethylamido)mono(iso-propylalkoxo)Niobium(V);

the Group 5 transition metal-containing precursor being tert-butylimidomethylcyclopentadienylmono(dimethylamido)mono(tert-butylalkoxo)Niobium(V);

the Group 5 transition metal-containing precursor being tert-amylimidocyclopentadienylmono(diethylamido)mono(iso-propylalkoxo)Niobium(V);

the Group 5 transition metal-containing precursor being tert-amylimidocyclopentadienylmono(diethylamido)mono(tert-butylalkoxo)Niobium(V);

the Group 5 transition metal-containing precursor being tert-butylimidocyclopentadienylmono(diethylamido)mono(iso-propylalkoxo)Tantalum(V);

the Group 5 transition metal-containing precursor being tert-butylimidocyclopentadienylmono(diethylamido)mono(tert-butylalkoxo)Tantalum(V);

the Group 5 transition metal-containing precursor being tert-butylimidocyclopentadienylmono(dimethylamido)mono(iso-propylalkoxo)Tantalum(V);

the Group 5 transition metal-containing precursor being tert-butylimidocyclopentadienylmono(dimethylamido)mono(tert-butylalkoxo)Tantalum(V);

the Group 5 transition metal-containing precursor being tert-butylimidomethylcyclopentadienylmono(diethylamido)mono(iso-propylalkoxo)Tantalum(V);

the Group 5 transition metal-containing precursor being tert-butylimidomethylcyclopentadienylmono(diethylamido)mono(tert-butylalkoxo)Tantalum(V);

the Group 5 transition metal-containing precursor being tert-butylimidomethylcyclopentadienylmono(dimethylamido)mono(iso-propylalkoxo)Tantalum(V);

the Group 5 transition metal-containing precursor being tert-butylimidomethylcyclopentadienylmono(dimethylamido)mono(tert-butylalkoxo)Tantalum(V);

the Group 5 transition metal-containing precursor being tert-amylimidocyclopentadienylmono(diethylamido)mono(iso-propylalkoxo)Tantalum(V);

the Group 5 transition metal-containing precursor being tert-amylimidocyclopentadienylmono(diethylamido)mono(tert-butylalkoxo)Tantalum(V);

NOTATION AND NOMENCLATURE

Certain abbreviations, symbols, and terms are used throughout the following description and claims, and include:

As used herein, the indefinite article "a" or "an" means one or more.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation, "Me," refers to a methyl group; the abbreviation, "Et," refers to an ethyl group; the abbreviation, "Pr," refers to a propyl group; the abbreviation, "iPr," refers to an isopropyl group; the abbreviation "Bu" refers to butyl; the abbreviation "tBu" refers to tert-butyl; the abbreviation "sBu" refers to sec-butyl; the abbreviation "Cp" refers to cyclopentadienyl; the abbreviation "Cp*" refers to pentamethylcyclopentadienyl; the abbreviation "op" refers to (open)pentadienyl.

The standard abbreviations of the elements from the periodic table of elements are used herein. It should be understood that elements may be referred to by these abbreviations (e.g., Si refers to silicon, N refers to nitrogen, O refers to oxygen, C refers to carbon, etc.)

BRIEF DESCRIPTION OF THE FIGURES

For a further understanding of the nature and objects of the present invention, reference should be made to the following detailed description, taken in conjunction with the accompanying figure wherein.

DESCRIPTION OF PREFERRED EMBODIMENTS

Disclosed are Group 5 transition metal-containing precursors having the formula:

$$\underset{R_5}{\overset{R_1}{\underset{|}{\overset{|}{\underset{\text{OR}_4}{\overset{N}{\underset{||}{M_{\text{\textbackslash\textbackslash\textbackslash}}\text{NR}_2\text{R}_3}}}}}}}$$

Formula 1), wherein M is selected from Group 5 transition metals consisting of V, Nb, and Ta and each of $R_1$, $R_2$, $R_3$, $R_4$, and $R_5$ are independently selected from H; a C1-C5 linear, branched, or cyclic alkyl group; a C1-C5 linear, branched, or cyclic alkylsilyl group (mono, bis, or tris alkyl); a C1-C5 linear, branched, or cyclic alkylamino group; or a C1-C5 linear, branched, or cyclic fluoroalkyl group. $R_2$ and $R_3$ can be identical or different, independently.

Exemplary Group 5 transition metal-containing precursor include but are not limited to:

the Group 5 transition metal-containing precursor being tert-butylimidocyclopentadienylmono(diethylamido)mono(iso-propylalkoxo)Vanadium(V);

the Group 5 transition metal-containing precursor being tert-butylimidocyclopentadienylmono(diethylamido)mono(tert-butylalkoxo)Vanadium(V);

the Group 5 transition metal-containing precursor being tert-butylimidocyclopentadienylmono(dimethylamido)mono(iso-propylalkoxo)Vanadium(V);

the Group 5 transition metal-containing precursor being tert-butylimidocyclopentadienylmono(dimethylamido)mono(tert-butylalkoxo)Vanadium(V);

the Group 5 transition metal-containing precursor being tert-butylimidomethylcyclopentadienylmono(diethylamido)mono(iso-propylalkoxo)Vanadium(V);

the Group 5 transition metal-containing precursor being tert-butylimidomethylcyclopentadienylmono(diethylamido)mono(tert-butylalkoxo)Vanadium(V);

the Group 5 transition metal-containing precursor being tert-butylimidomethylcyclopentadienylmono(dimethylamido)mono(iso-propylalkoxo)Vanadium(V);

the Group 5 transition metal-containing precursor being tert-butylimidomethylcyclopentadienylmono(dimethylamido)mono(tert-butylalkoxo)Vanadium(V);

the Group 5 transition metal-containing precursor being tert-amylimidocyclopentadienylmono(diethylamido)mono(iso-propylalkoxo)Vanadium(V);

the Group 5 transition metal-containing precursor being tert-amylimidocyclopentadienylmono(diethylamido)mono(tert-butylalkoxo)Vanadium(V);

the Group 5 transition metal-containing precursor being tert-amylimidocyclopentadienylmono(dimethylamido)mono(iso-propylalkoxo)Vanadium(V);

the Group 5 transition metal-containing precursor being tert-amylimidocyclopentadienylmono(dimethylamido)mono(tert-butylalkoxo)Vanadium(V);

the Group 5 transition metal-containing precursor being tert-butylimidocyclopentadienylmono(diethylamido)mono(iso-propylalkoxo)Niobium(V);

the Group 5 transition metal-containing precursor being tert-butylimidocyclopentadienylmono(diethylamido)mono(tert-butylalkoxo)Niobium(V);

the Group 5 transition metal-containing precursor being tert-butylimidocyclopentadienylmono(dimethylamido)mono(iso-propylalkoxo)Niobium(V);

the Group 5 transition metal-containing precursor being tert-butylimidocyclopentadienylmono(dimethylamido)mono(tert-butylalkoxo)Niobium(V);

the Group 5 transition metal-containing precursor being tert-butylimidomethylcyclopentadienylmono(diethylamido)mono(iso-propylalkoxo)Niobium(V);

the Group 5 transition metal-containing precursor being tert-butylimidomethylcyclopentadienylmono(diethylamido)mono(tert-butylalkoxo)Niobium(V);

the Group 5 transition metal-containing precursor being tert-butylimidomethylcyclopentadienylmono(dimethylamido)mono(iso-propylalkoxo)Niobium(V);

the Group 5 transition metal-containing precursor being tert-butylimidomethylcyclopentadienylmono(dimethylamido)mono(tert-butylalkoxo)Niobium(V);

the Group 5 transition metal-containing precursor being tert-amylimidocyclopentadienylmono(diethylamido)mono(iso-propylalkoxo)Niobium(V);

the Group 5 transition metal-containing precursor being tert-amylimidocyclopentadienylmono(diethylamido)mono(tert-butylalkoxo)Niobium(V);

the Group 5 transition metal-containing precursor being tert-butylimidocyclopentadienylmono(diethylamido)mono(iso-propylalkoxo)Tantalum(V);

the Group 5 transition metal-containing precursor being tert-butylimidocyclopentadienylmono(diethylamido)mono(tert-butylalkoxo)Tantalum(V);

the Group 5 transition metal-containing precursor being tert-butylimidocyclopentadienylmono(dimethylamido)mono(iso-propylalkoxo)Tantalum(V);

the Group 5 transition metal-containing precursor being tert-butylimidocyclopentadienylmono(dimethylamido)mono(tert-butylalkoxo)Tantalum(V);

the Group 5 transition metal-containing precursor being tert-butylimidomethylcyclopentadienylmono(diethylamido)mono(iso-propylalkoxo)Tantalum(V);

the Group 5 transition metal-containing precursor being tert-butylimidomethylcyclopentadienylmono(diethylamido)mono(tert-butylalkoxo)Tantalum(V);

the Group 5 transition metal-containing precursor being tert-butylimidomethylcyclopentadienylmono(dimethylamido)mono(iso-propylalkoxo)Tantalum(V);

the Group 5 transition metal-containing precursor being tert-butylimidomethylcyclopentadienylmono(dimethylamido)mono(tert-butylalkoxo)Tantalum(V);

the Group 5 transition metal-containing precursor being tert-amylimidocyclopentadienylmono(diethylamido)mono(iso-propylalkoxo)Tantalum(V);

the Group 5 transition metal-containing precursor being tert-amylimidocyclopentadienylmono(diethylamido)mono(tert-butylalkoxo)Tantalum(V);

Preferably, the Group 5 transition metal-containing precursor is tert-butylimidocyclopentadienylmono(dimethylamido)mono(tert-butylalkoxo)Niobium(V), due to its excellent vaporization results in atmospheric thermogravimetric analysis, leaving a small amount of final residue.

The disclosed Group 5 transition metal-containing precursors may be synthesized by reacting the corresponding alcohols with the corresponding imidocyclopentadienyl-bis-amido Group 5 transition metal in a suitable solvent, such as THF and ether. An exemplary synthesis method containing further details is provided in the Examples that follow.

Also disclosed are methods for forming a Group 5 transition metal-containing layer on a substrate using a vapor deposition process. The method may be useful in the manufacture of semiconductor, photovoltaic, LCD-TFT, or flat panel type devices. The disclosed Group 5 transition metal-containing precursors may be used to deposit thin Group 5 transition metal-containing films using any deposition methods known to those of skill in the art. Examples of suitable deposition methods include without limitation, conventional chemical vapor deposition (CVD), atomic layer deposition (ALD), or other types of depositions that are related to vapor coating such as a plasma enhanced CVD (PECVD), plasma enhanced ALD (PEALD), pulsed CVD (PCVD), low pressure CVD (LPCVD), sub-atmospheric CVD (SACVD) or atmospheric pressure CVD (APCVD), hot-wire CVD (HW-CVD, also known as cat-CVD, in which a hot wire serves as an energy source for the deposition process), spatial ALD, hot-wire ALD (HWALD), radicals incorporated deposition, and super critical fluid deposition or combinations thereof. The deposition method is preferably ALD, PE-ALD, or spatial ALD in order to provide suitable step coverage and film thickness control.

The disclosed Group 5 transition metal-containing precursors may be supplied either in neat form or in a blend with a suitable solvent, such as ethyl benzene, xylene, mesitylene, decane, dodecane. The disclosed precursors may be present in varying concentrations in the solvent.

One or more of the neat or blended Group 5 transition metal-containing precursors are introduced into a reactor in vapor form by conventional means, such as tubing and/or flow meters. The precursor in vapor form may be produced by vaporizing the neat or blended precursor solution through a conventional vaporization step such as direct vaporization, distillation, or by bubbling. The neat or blended precursor may be fed in liquid state to a vaporizer where it is vaporized before it is introduced into the reactor. Alternatively, the neat or blended precursor may be vaporized by passing a carrier gas into a container containing the precursor or by bubbling the carrier gas into the precursor. The carrier gas may include, but is not limited to, Ar, He, $N_2$, and mixtures thereof. Bubbling with a carrier gas may also remove any dissolved oxygen present in the neat or blended precursor solution. The carrier gas and precursor are then introduced into the reactor as a vapor.

If necessary, the container of disclosed precursor may be heated to a temperature that permits the precursor to be in its liquid phase and to have a sufficient vapor pressure. The container may be maintained at temperatures in the range of, for example, approximately 0° C. to approximately 150° C. Those skilled in the art recognize that the temperature of the container may be adjusted in a known manner to control the amount of precursor vaporized.

The reactor may be any enclosure or chamber within a device in which deposition methods take place such as without limitation, a parallel-plate type reactor, a cold-wall type reactor, a hot-wall type reactor, a single-wafer reactor, a multi-wafer reactor, or other types of deposition systems under conditions suitable to cause the precursors to react and form the layers.

Generally, the reactor contains one or more substrates onto which the thin films will be deposited. The one or more substrates may be any suitable substrate used in semiconductor, photovoltaic, flat panel, or LCD-TFT device manufacturing. Examples of suitable substrates include without limitation, silicon substrates, silica substrates, silicon nitride substrates, silicon oxy nitride substrates, tungsten substrates, or combinations thereof. Plastic substrates, such as poly(3,4-ethylenedioxythiophene)poly (styrenesulfonte) [PEDOT:PSS], may also be used. Additionally, substrates comprising tungsten or noble metals (e.g. platinum, palladium, rhodium, or gold) may be used. The substrate may also have one or more layers of differing materials already deposited upon it from a previous manufacturing step.

The temperature and the pressure within the reactor are held at conditions suitable for ALD or CVD depositions. In other words, after introduction of the vaporized precursor into the chamber, conditions within the chamber are such that at least part of the vaporized precursor is deposited onto the substrate to form a Group 5 transition metal-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 150° C. and about 350° C.

The temperature of the reactor may be controlled by either controlling the temperature of the substrate holder or controlling the temperature of the reactor wall. Devices used to heat the substrate are known in the art. The reactor wall is heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 150° C. to approximately 350° C. Alternatively, when a thermal process is performed, the deposition temperature may range from approximately 200° C. to approximately 500° C.

In addition to the disclosed precursor, a reactant may also be introduced into the reactor. The reactant may be an oxidizing gas such as one of $O_2$, $O_3$, $H_2O$, $H_2O_2$, NO, $N_2O$, $NO_2$, oxygen containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as O. or OH., and mixtures thereof. Alternatively, the reactant may be a reducing gas such as one of $H_2$, $H_2CO$, $NH_3$, $SiH_4$, $Si_2H_6$, $Si_3H_8$, $(CH_3)_2SiH_2$, $(C_2H_5)_2SiH_2$, $(CH_3)SiH_3$, $(C_2H_5)SiH_3$, phenyl silane, $N_2H_4$, $N(SiH_3)_3$, $N(CH_3)H_2$, $N(C_2H_5)H_2$, $N(CH_3)_2H$, $N(C_2H_5)_2H$, $N(CH_3)_3$, $N(C_2H_5)_3$, $(SiMe_3)_2NH$, $(CH_3)HNNH_2$, $(CH_3)_2NNH_2$, phenyl hydrazine, N-containing molecules, $B_2H_6$, 9-borabicyclo[3,3,1]nonane, dihydrobenzenfuran, pyrazoline, trimethylaluminium, dimethylzinc, diethylzinc, radical species thereof, and mixtures thereof. Preferably, the reducing as is $H_2$, $NH_3$, $SiH_4$, $Si_2H_6$, $Si_3H_8$, $SiH_2Me_2$, $SiH_2Et_2$, $N(SiH_3)_3$, hydrogen radicals thereof, or mixtures thereof.

The reactant may be treated by a plasma, in order to decompose the reactant into its radical form. $N_2$ may also be utilized as a reducing gas when treated with plasma. For instance, the plasma may be generated with a power ranging from about 50 W to about 500 W, preferably from about 100 W to about 200 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

The vapor deposition conditions within the chamber allow the disclosed precursor and the reactant to react and form a Group 5 transition metal-containing film on the substrate. In some embodiments, Applicants believe that plasma-treating the reactant may provide the reactant with the energy needed to react with the disclosed precursor.

Depending on what type of film is desired to be deposited, a second precursor may be introduced into the reactor. The second precursor may be used to provide additional elements to the Group 5 transition metal-containing film. The additional elements may include copper, praseodymium, manganese, ruthenium, titanium, tantalum, bismuth, zirconium, hafnium, lead, vanadium, niobium, tantalum, magnesium, aluminum, lanthanum, or mixtures of these. When a second precursor is utilized, the resultant film deposited on the substrate may contain Group 5 transition metal in combination with at least one additional element.

The Group 5 transition metal-containing precursors and reactants may be introduced into the reactor either simultaneously (chemical vapor deposition), sequentially (atomic layer deposition) or different combinations thereof. The reactor may be purged with an inert gas between the introduction of the precursor and the introduction of the reactant. Alternatively, the reactant and the precursor may be mixed together to form a reactant/precursor mixture, and then introduced to the reactor in mixture form. Another example is to introduce the reactant continuously and to introduce the at least one Group 5 transition metal-containing precursor by pulse (pulsed chemical vapor deposition).

The vaporized precursor and the reactant may be pulsed sequentially or simultaneously (e.g. pulsed CVD) into the reactor. Each pulse of precursor may last for a time period ranging from about 0.01 seconds to about 10 seconds, alternatively from about 0.3 seconds to about 3 seconds, alternatively from about 0.5 seconds to about 2 seconds. In another embodiment, the reactant may also be pulsed into the reactor. In such embodiments, the pulse of each gas may last for a time period ranging from about 0.01 seconds to about 10 seconds, alternatively from about 0.3 seconds to about 3 seconds, alternatively from about 0.5 seconds to about 2 seconds.

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed Group 5 transition metal-containing precursor and a reactant are simultaneously introduced into the reactor. The two react to form the resulting Group 5 transition metal-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed Group 5 transition metal-containing precursor is introduced into the reactor, where it is contacted with a suitable substrate. Excess precursor may then be removed from the reactor by purging and/or evacuating the reactor. A desired gas (for example, $O_3$) is introduced into the reactor where it reacts with the absorbed precursor in a self-limiting manner. Any excess reducing gas is removed from the reactor by purging and/or evacuating the reactor. If the desired film is a Group 5 transition metal film, this two-step process may provide the desired film thickness or may be repeated until a film having the necessary thickness has been obtained.

Alternatively, if the desired film contains Group 5 transition metal and a second element, the two-step process above may be followed by introduction of the vapor of a second precursor into the reactor. The second precursor will be selected based on the nature of the Group 5 transition metal film being deposited. After introduction into the reactor, the second precursor is contacted with the substrate. Any excess second precursor is removed from the reactor by purging and/or evacuating the reactor. Once again, a desired gas may be introduced into the reactor to react with the second precursor. Excess gas is removed from the reactor by purging and/or evacuating the reactor. If a desired film thickness has been achieved, the process may be terminated. However, if a thicker film is desired, the entire four-step process may be repeated. By alternating the provision of the Group 5 transition metal-containing precursor, second precursor, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

The Group 5 transition metal-containing films resulting from the processes discussed above may include a pure Group 5 transition metal (M=V, Nb, Ta), Group 5 transition metal silicide ($M_kSi_l$), or Group 5 transition metal oxide ($M_nO_m$), Group 5 transition metal nitride ($M_oN_p$) film wherein k, l, m, n, o and p are integers which inclusively range from 1 to 6. One of ordinary skill in the art will recognize that by judicial selection of the appropriate disclosed precursor, optional second precursors, and reactant species, the desired film composition may be obtained.

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Group 5 transition metal-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Group 5 transition metal-containing film. This in turn tends to improve the resistivity of the film.

EXAMPLES

The following examples illustrate experiments performed in conjunction with the disclosure herein. The examples are not intended to be all inclusive and are not intended to limit the scope of disclosure described herein.

Example 1

(tert-BuN=)NbCp(NMe$_2$)(OtBu) Synthesis

To a solution of tert-BuN=NbCp(NMe$_2$)$_3$ (2 g, 6.30 mmol) in ca. 30 mL of THF at −78° C., was added dropwise a solution of tBuOH (0.47 g, 6.34 mmol) in THF. The mixture was slowly warmed to room temperature and stirred overnight. Solvent was then removed under vacuum to give a yellow liquid. The material was purified by distillation at 120° C. @ 170 mTorr (bp~80-94° C.) to give 1.43 g (66%) of a yellow oil.

Figure 1:
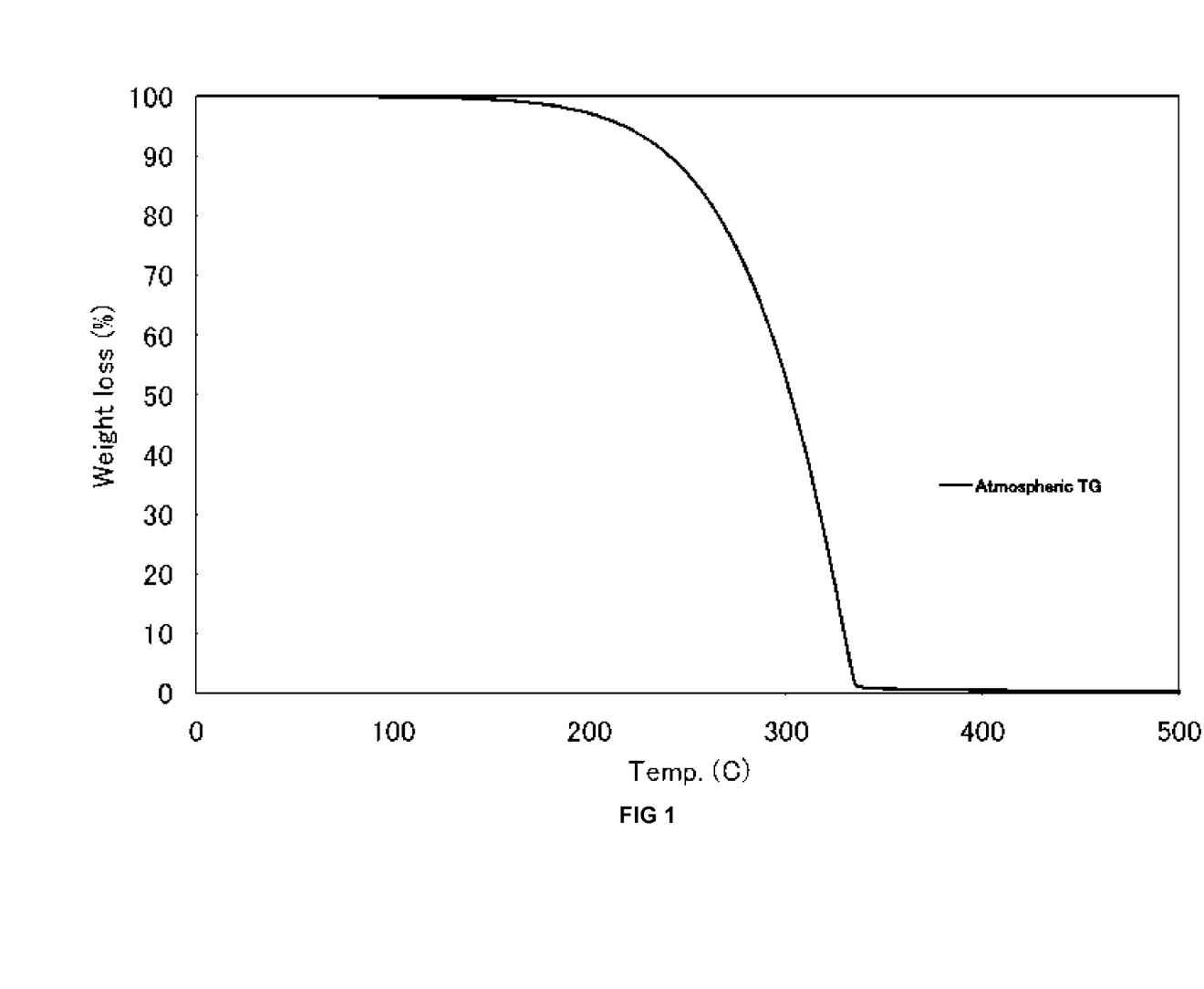
FIG. 1 is a ThermoGravimetric Analysis (TGA) demonstrating the percentage of weight loss (TGA) with increasing temperature of tert-BuN=NbCp(NEt$_2$)(OtBu).
Figure 2:
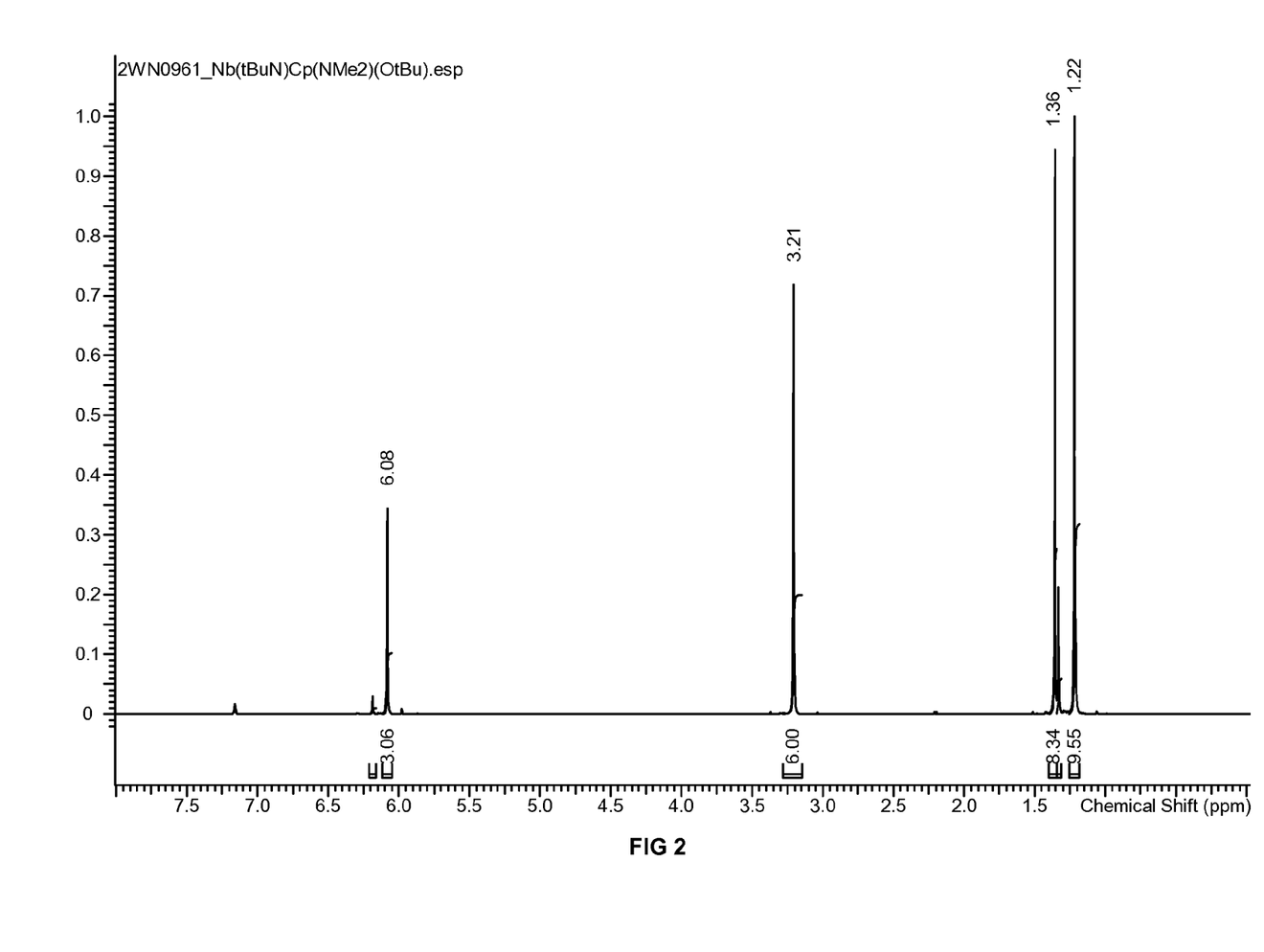
FIG. 2 is a $^1$HNMR spectrum of tert-BuN=NbCp(NEt$_2$)(OtBu).

The oil left a <1% residual mass during TGA analysis measured at a temperature rising rate of 10° C./min in an atmosphere which flows nitrogen at 200 mL/min. These results are depicted in FIG. 1, which is a TGA graph demonstrating the percentage of weight loss with temperature change. The NMR1H spectrum is provided in FIG. 2.

NMR1H (δ, ppm, C6D6): 6.08 (s, 5H), 3.21 (s, 6H), 1.38 (s, 9H), 1.21 (s, 9H).

Example 2

ALD of Group 5 Transition Metal

ALD tests were performed using the (tert-BuN═)NbCp (NMe$_2$)(OtBu) prepared in Example 1, which was placed in a vessel heated up to 90° C. Typical ALD conditions were used with a reactor pressure fixed at ~1 Torr. ALD behavior with complete surface saturation and reaction was assessed in a temperature window of 200-400° C. on pure silicon wafers.

A deposition rate was obtained at 200-400°. After annealing the film, X-ray Photoelectron Spectroscopy (XPS) was used to detect impurities incorporated into the film. The Scanning Electron Microscope (SEM) showed a surface with uniform and smooth grains, and with continuity. Depositions performed on a patterned wafer with trenches allowed the formation of a film with a good conformality It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A transition metal-containing precursor having the formula:

Formula 1), wherein M is selected from the group consisting of V and Ta and each of $R_1$, $R_2$, $R_3$, $R_4$, and $R_5$ is independently selected from the group consisting of H; a C1-C5 linear, branched, or cyclic alkyl group; a C1-C5 linear, branched, or cyclic alkylsilyl group; a C1-C5 linear, branched, or cyclic alkylamino group; and a C1-C5 linear, branched, or cyclic fluoroalkyl group.

2. The transition metal-containing precursor of claim 1, wherein $R_2$ and $R_3$ are the same.

3. The transition metal-containing precursor of claim 1, wherein the transition metal-containing precursor is selected from the group consisting of:
tert-butylimidocyclopentadienylmono(diethylamido) mono(iso-propylalkoxo)Vanadium(V);
tert-butylimidocyclopentadienylmono(diethylamido) mono(tert-butylalkoxo)Vanadium(V);
tert-butylimidocyclopentadienylmono(dimethylamido) mono(iso-propylalkoxo)Vanadium(V);
tert-butylimidocyclopentadienylmono(dimethylamido) mono(tert-butylalkoxo)Vanadium(V);
tert-butylimidomethylcyclopentadienylmono(diethylamido)mono(iso-propylalkoxo)Vanadium(V);
tert-butylimidomethylcyclopentadienylmono(diethylamido)mono(tert-butylalkoxo)Vanadium(V);
tert-butylimidomethylcyclopentadienylmono(dimethylamido)mono(iso-propylalkoxo)Vanadium(V);
tert-butylimidomethylcyclopentadienylmono(dimethylamido)mono(tert-butylalkoxo)Vanadium(V);
tert-amylimidocyclopentadienylmono(diethylamido) mono(iso-propylalkoxo)Vanadium(V);
tert-amylimidocyclopentadienylmono(diethylamido) mono(tert-butylalkoxo)Vanadium(V);
tert-amylimidocyclopentadienylmono(dimethylamido) mono(iso-propylalkoxo)Vanadium(V);
tert-amylimidocyclopentadienylmono(dimethylamido) mono(tert-butylalkoxo)Vanadium(V);
tert-butylimidocyclopentadienylmono(diethylamido) mono(iso-propylalkoxo)Tantalum(V);
tert-butylimidocyclopentadienylmono(diethylamido) mono(tert-butylalkoxo)Tantalum(V);
tert-butylimidocyclopentadienylmono(dimethylamido) mono(iso-propylalkoxo)Tantalum(V);
tert-butylimidocyclopentadienylmono(dimethylamido) mono(tert-butylalkoxo)Tantalum(V);
tert-butylimidomethylcyclopentadienylmono(diethylamido)mono(iso-propylalkoxo)Tantalum(V);
tert-butylimidomethylcyclopentadienylmono(diethylamido)mono(tert-butylalkoxo)Tantalum(V);
tert-butylimidomethylcyclopentadienylmono(dimethylamido)mono(iso-propylalkoxo)Tantalum(V);
tert-butylimidomethylcyclopentadienylmono(dimethylamido)mono(tert-butylalkoxo)Tantalum(V);
tert-amylimidocyclopentadienylmono(diethylamido) mono(iso-propylalkoxo)Tantalum(V); and
tert-amylimidocyclopentadienylmono(diethylamido) mono(tert-butylalkoxo)Tantalum(V).

4. The transition metal-containing precursor of claim 2, wherein the transition metal-containing precursor is tert-butylimidocyclopentadienyl mono(dimethylamino)mono (tert-butylalkoxo)Tantalum(V).

5. A process for the deposition of a transition metal-containing film on a substrate, comprising:
introducing at least one transition metal-containing precursor into a reactor having at least one substrate disposed therein, the at least one transition metal-containing precursor having the following formula:

wherein M is selected from the group consisting of V, and Ta and each of $R_1$, $R_2$, $R_3$, $R_4$, and $R_5$ is independently selected from H; a C1-C5 linear, branched, or cyclic alkyl group; a C1-C5 linear, branched, or cyclic alkylsilyl group; a C1-C5 linear, branched, or cyclic alkylamino group; and a C1-C5 linear, branched, or cyclic fluoroalkyl group; and depositing at least part of the at least one transition metal-containing precursor onto the at least one substrate to form the transition metal-containing film using a vapor deposition method.

6. The process of claim 5, further comprising introducing at least one reactant into the reactor.

7. The process of claim 6, wherein the reactant is selected from the group consisting of $H_2$, $H_2CO$ $N_2H_4$, $NH_3$, $SiH_4$, $Si_2H_6$, $Si_3H_8$, $SiH_2Me_2$, $SiH_2Et_2$, $N(SiH_3)_3$, hydrogen radicals thereof; and mixtures thereof.

8. The process of claim 6, wherein the reactant is selected from the group consisting of: $O_2$, $O_3$, $H_2O$, $H_2O_2$ NO, $N_2O$, $NO_2$, oxygen radicals thereof; and mixtures thereof.

9. The process of claim 6, wherein the transition metal-containing precursor and the reactant are introduced into the reactor sequentially.

10. The process of claim 5, wherein the vapor deposition method is chemical vapor deposition.

11. The process of claim 6, wherein the transition metal-containing precursor and the reactant are introduced into the reactor sequentially.

12. The process of claim 5, wherein the vapor deposition method is atomic layer deposition.

13. The process of claim 5, wherein the transition metal-containing precursor is selected from the group consisting of:

tert-butylimidocyclopentadienylmono(diethylamido) mono(iso-propylalkoxo)Vanadium(V);
tert-butylimidocyclopentadienylmono(diethylamido) mono(tert-butylalkoxo)Vanadium(V);
tert-butylimidocyclopentadienylmono(dimethylamido) mono(iso-propylalkoxo)Vanadium(V);
tert-butylimidocyclopentadienylmono(dimethylamido) mono(tert-butylalkoxo)Vanadium(V);
tert-butylimidomethylcyclopentadienylmono(diethylamido)mono(iso-propylalkoxo)Vanadium(V);
tert-butylimidomethylcyclopentadienylmono(diethylamido)mono(tert-butylalkoxo)Vanadium(V);
tert-butylimidomethylcyclopentadienylmono(dimethylamido)mono(iso-propylalkoxo)Vanadium(V);
tert-butylimidomethylcyclopentadienylmono(dimethylamido)mono(tert-butylalkoxo)Vanadium(V);
tert-amylimidocyclopentadienylmono(diethylamido) mono(iso-propylalkoxo)Vanadium(V);
tert-amylimidocyclopentadienylmono(diethylamido) mono(tert-butylalkoxo)Vanadium(V);
tert-amylimidocyclopentadienylmono(dimethylamido) mono(iso-propylalkoxo)Vanadium(V);
tert-amylimidocyclopentadienylmono(dimethylamido) mono(tert-butylalkoxo)Vanadium(V);
tert-butylimidocyclopentadienylmono(diethylamido) mono(iso-propylalkoxo)Tantalum(V);
tert-butylimidocyclopentadienylmono(diethylamido) mono(tert-butylalkoxo)Tantalum(V);
tert-butylimidocyclopentadienylmono(dimethylamido) mono(iso-propylalkoxo)Tantalum(V);
tert-butylimidocyclopentadienylmono(dimethylamido) mono(tert-butylalkoxo)Tantalum(V);
tert-butylimidomethylcyclopentadienylmono(diethylamido)mono(iso-propylalkoxo)Tantalum(V);
tert-butylimidomethylcyclopentadienylmono(diethylamido)mono(tert-butylalkoxo)Tantalum(V);
tert-butylimidomethylcyclopentadienylmono(dimethylamido)mono(iso-propylalkoxo)Tantalum(V);
tert-butylimidomethylcyclopentadienylmono(dimethylamido)mono(tert-butylalkoxo)Tantalum(V);
tert-amylimidocyclopentadienylmono(diethylamido) mono(iso-propylalkoxo)Tantalum(V); and
tert-amylimidocyclopentadienylmono(diethylamido) mono(tert-butylalkoxo)Tantalum(V).

14. The process of claim 13, wherein the transition metal-containing precursor is tert-butylimidocyclopentadienylmono(dimethylamido)mono(tert-butylalkoxo)Niobium (V) or tert-butylimidocyclopentadienylmono(dimethylamido)mono(tert-butylalkoxo)Tantalum(V).

15. A transition metal-containing precursor having the formula:

Formula 1), wherein M is Nb and each of $R_1$, $R_2$, $R_3$, $R_4$, and $R_5$ is independently selected from the group consisting of H; a C1-C5 linear, branched, or cyclic alkyl group; a C1-C5 linear, branched, or cyclic alkylsilyl group; a C1-C5 linear, branched, or cyclic alkylamino group; and a C1-C5 linear, branched, or cyclic fluoroalkyl group, provided that $R_2$ and $R_3$ are the same.

16. The transition metal-containing precursor of claim 15, wherein the transition metal-containing precursor is selected from the group consisting of:

tert-butylimidocyclopentadienylmono(diethylamido) mono(iso-propylalkoxo)Niobium(V);
tert-butylimidocyclopentadienylmono(diethylamido) mono(tert-butylalkoxo)Niobium(V);
tert-butylimidocyclopentadienylmono(dimethylamido) mono(iso-propylalkoxo)Niobium(V);
tert-butylimidocyclopentadienylmono(dimethylamido) mono(tert-butylalkoxo)Niobium(V);
tert-butylimidomethylcyclopentadienylmono(diethylamido)mono(iso-propylalkoxo)Niobium(V);
tert-butylimidomethylcyclopentadienylmono(diethylamido)mono(tert-butylalkoxo)Niobium(V);
tert-butylimidomethylcyclopentadienylmono(dimethylamido)mono(iso-propylalkoxo)Niobium(V);
tert-butylimidomethylcyclopentadienylmono(dimethylamido)mono(tert-butylalkoxo)Niobium(V);
tert-amylimidocyclopentadienylmono(diethylamido) mono(iso-propylalkoxo)Niobium(V); and
tert-amylimidocyclopentadienylmono(diethylamido) mono(tert-butylalkoxo)Niobium(V).

17. The transition metal-containing precursor of claim 15, wherein the transition metal-containing precursor is tert-butylimidocyclopentadienylmono(dimethylamino)mono (tert-butylalkoxo)Niobium(V).

18. A process for the deposition of a transition metal-containing film on a substrate, comprising:
introducing at least one transition metal-containing precursor into a reactor having at least one substrate disposed therein, the at least one transition metal-containing precursor having the following formula:

wherein M is Nb and each of $R_1$, $R_2$, $R_3$, $R_4$, and $R_5$ is independently selected from H; a C1-C5 linear, branched, or cyclic alkyl group; a C1-C5 linear, branched, or cyclic alkylsilyl group; a C1-C5 linear, branched, or cyclic alkylamino group; and a C1-C5 linear, branched, or cyclic fluoroalkyl group, provided that $R_2$ and $R_3$ are the same; and
depositing at least part of the at least one transition metal-containing precursor onto the at least one substrate to form the transition metal-containing film using a vapor deposition method.

19. The process of claim 5, further comprising introducing at least one reactant into the reactor.

20. The transition metal-containing precursor of claim 18, wherein the transition metal-containing precursor is selected from the group consisting of:
  tert-butylimidocyclopentadienylmono(diethylamido) mono(iso-propylalkoxo)Niobium(V);
  tert-butylimidocyclopentadienylmono(diethylamido) mono(tert-butylalkoxo)Niobium(V);
  tert-butylimidocyclopentadienylmono(dimethylamido) mono(iso-propylalkoxo)Niobium(V);
  tert-butylimidocyclopentadienylmono(dimethylamido) mono(tert-butylalkoxo)Niobium(V);
  tert-butylimidomethylcyclopentadienylmono(diethylamido)mono(iso-propylalkoxo)Niobium(V);
  tert-butylimidomethylcyclopentadienylmono(diethylamido)mono(tert-butylalkoxo)Niobium(V);
  tert-butylimidomethylcyclopentadienylmono(dimethylamido)mono(iso-propylalkoxo)Niobium(V);
  tert-butylimidomethylcyclopentadienylmono(dimethylamido)mono(tert-butylalkoxo)Niobium(V);
  tert-amylimidocyclopentadienylmono(diethylamido) mono(iso-propylalkoxo)Niobium(V); and
  tert-amylimidocyclopentadienylmono(diethylamido) mono(tert-butylalkoxo)Niobium(V).

* * * * *